United States Patent [19]

Pesa et al.

[11] 4,250,093

[45] Feb. 10, 1981

[54] PROCESS FOR THE PREPARATION OF LAOTAMS

[75] Inventors: Frederick A. Pesa, Twinsburg; Anne M. Graham, Northfield, both of Ohio

[73] Assignee: The Standard Oil Company (Ohio)

[21] Appl. No.: 53,606

[22] Filed: Jun. 29, 1979

[51] Int. Cl.$^3$ ............................................. C07D 201/08
[52] U.S. Cl. ............................ 260/239.3 A; 546/243;
260/326.5 FN; 260/464; 260/465 D; 260/465.4
[58] Field of Search .............. 260/239.3 A, 326.5 FN;
546/243

[56] References Cited

U.S. PATENT DOCUMENTS

| | | | |
|---|---|---|---|
| 2,843,600 | 7/1958 | McKeever | 260/326.5 FN |
| 3,919,197 | 11/1975 | Garritsen et al. | 260/239.3 A |
| 3,931,292 | 1/1976 | Garritsen et al. | 260/239.3 A |

FOREIGN PATENT DOCUMENTS

| | | | |
|---|---|---|---|
| 1035139 | 7/1958 | Fed. Rep. of Germany | 260/239.3 A |
| 1307065 | 2/1973 | United Kingdom | 546/243 |

*Primary Examiner*—Henry R. Jiles
*Assistant Examiner*—Robert T. Bond
*Attorney, Agent, or Firm*—Joseph G. Curatolo; Herbert D. Knudsen; Larry W. Evans

[57] ABSTRACT

Five, six and seven member nitrogen-containing saturated heterocyclic compounds can be prepared by the catalytic hydrogenation/cyclization of beta, gamma and delta-cyanoesters. Applicants have discovered that this reaction is especially effective when it is conducted in the presence of catalysts comprising at least one of ruthenium and iron.

26 Claims, No Drawings

PROCESS FOR THE PREPARATION OF LAOTAMS

BACKGROUND OF THE INVENTION

There are several known methods for producing the heterocyclic compounds of this invention. The five membered heterocyclic compound, pyrrolidone, can be produced by the hydrogenation of methyl beta-cyanopropionate (U.S. Pat. No. 2,843,600). This patent discloses that at temperatures above 150° pyrrolidone is obtained by slowly contacting an alkyl beta-cyanopropionate with a Raney nickel catalyst. Seven membered nitrogen-containing rings, e.g. caprolactam, are normally prepared from phenol via cyclohexanone oxime. The cyclohexanone oxime is converted to caprolactam by the Beckman rearrangement (see Encyclopedia of Chemical Technology, Kirk-Othmer, Vol. 16 (Second Edition 1968)).

The above methods are each disadvantageous for some reason. First, the catalysts used therein are prone to deactivation. Second, the processes must be conducted in the presence of a large amount of $NH_3$ and at very high catalyst concentrations. The instant process, on the other hand, can be conducted continuously at low catalyst to hydrocarbon ratios in the absence of ammonia. Furthermore, the inventive catalysts have long active lifes and result in high yields and selectivities of the desired product.

SUMMARY OF THE INVENTION

The instant invention provides a process for producing a five, six or seven-membered saturated nitrogen-containing heterocyclic compound comprising contacting a beta, gamma or delta-cyanoester with hydrogen in the presence of a catalyst comprising at least one of ruthenium and iron.

In one embodiment, this invention provides a process for the production of five-membered nitrogen-containing heterocyclic compounds comprising hydrogenating a beta-cyanoester in the presence of an oxide complex catalyst comprising ruthenium and iron. In another embodiment, this invention provides a process for the production of seven-membered nitrogen-containing heterocyclic compounds comprising hydrogenating a delta-cyanoester in the presence of an oxide complex catalyst comprising ruthenium and iron.

DETAILED DESCRIPTION

In accordance with the present invention, improved yields and selectivities of five, six and seven membered nitrogen-containing heterocyclic compounds are obtained by hydrogenating a cyanoester in the presence of a catalyst comprising at least one of ruthenium and iron. The overall reaction taking place in this process is represented by the following equations:

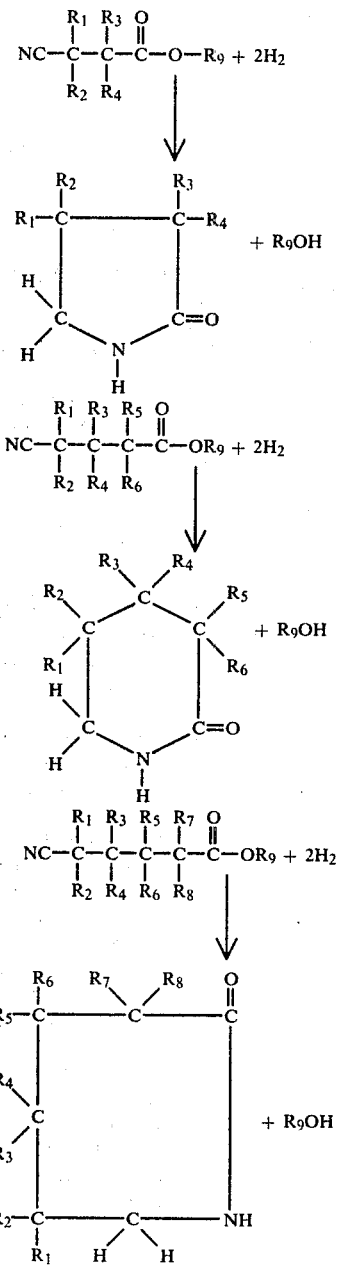

wherein $R_1$, $R_2$, $R_3$, $R_4$, $R_5$, $R_6$, $R_7$, $R_8$ and $R_9$ are defined below.

Reactants

Generally, any beta, gamma or delta-cyanoester can be employed as a reactant in the inventive process. However, steric hindrance may become a factor and the reaction rate may be reduced if the cyanoester is substituted with a bulky group.

Preferred cyanoester compounds which are useful in the instant process have the following structure:

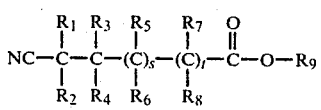

wherein s and t are 0 or 1; and wherein $R_1$, $R_2$, $R_3$, $R_4$, $R_5$, $R_6$, $R_7$ and $R_8$ are each independently selected from:
(1) hydrogen;
(2) $C_{1-4}$ alkyl;
(3) $-(CH_2)_n-O-(CH_2)_r-H$, wherein n and r are each independently 0-4;

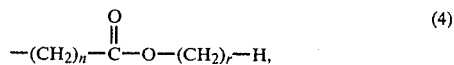

wherein n and r are each independently 0-4; and wherein $R_9$ is selected from:
(1) $C_{1-30}$ alkyls; and
(2) carbocyclic radicals containing up to 30 carbon atoms.

Preferably, the cyanoester comprises compounds wherein $R_1$, $R_2$, $R_3$, $R_4$, $R_5$, $R_6$, $R_7$, and $R_8$ are each independently selected from:
(1) hydrogen;
(2) methyl;
and wherein $R_9$ is selected from the group consisting of:
(1) $C_{1-4}$ alkyls;
(2) phenyl.

Most preferably, the cyanoester comprises compounds wherein $R_1$, $R_2$, $R_3$, $R_4$, $R_5$, $R_6$, $R_7$, and $R_8$ are each independently selected from hydrogen and wherein $R_9$ is selected from the group consisting of $C_{1-4}$ alkyls.

Since there is already a large commercial market for pyrrolidone, i.e. the five membered ring, and caprolactam, i.e. the seven membered ring, s and t are preferably both 0 or both 1.

Examples of reactants which are within the scope of this invention are methyl-beta-cyanopropionate, 4-cyanobutyrate and 5-cyano-valerate. A process for producing these cyanoesters is disclosed in U.S. Pat. Ser. No. 973,069, filed Dec. 26, 1978.

The amount of hydrogen in the reaction system is not critical, the reaction will proceed as long as any amount of hydrogen is present. It is preferred to have at least two moles of hydrogen per mole of cyanoester. If desired, a carrier gas which is inert to the reactants, products and catalyst can be included in the reaction system.

Furthermore, any material which is inert to the reactants, catalyst and products of this reaction may be included with the cyanoester as a diluent. For example, methanol or ethanol could be added to the reaction system, if desired.

Process Conditions

In carrying out the inventive process, the cyanoester and hydrogen are contacted in the presence of the catalyst described below for effecting the hydrogenation/cyclization reaction. This reaction can be accomplished both in the batch mode and continuously in either the gas phase or liquid phase.

The reaction temperature is normally maintained between 50° C. and 200° C., preferably 75° C. to 125° C., and most preferably around 100° C. The reaction pressure is normally maintained between 100 and 2,000 psi, and preferably between 500 to 1,200 psi. When the reaction is carried out in the batch mode, the reactants and catalysts are contacted with one another for a period of about 10 minutes to 6 hours, and preferably ½ hour to 3 hours. A reaction time of less than 10 minutes or more than 6 hours can be used if desired although better results will be obtained if the reaction time is maintained within this range. When the process is carried out on a continuous basis, the reactant catalyst contact time is normally 10 seconds to 10 minutes, preferably 100 seconds to 5 minutes.

Catalyst

Any catalyst comprising at least one of ruthenium and iron may be employed in the instant process. In particular, both active catalytic metal catalysts and oxide complex catalysts are effective in this invention.

The oxide complex catalyst useful in this invention can be represented by the following formula:

wherein
A is selected from the group consisting of Co, Ni, Rh, Pd, Os, Ir, Pt and mixtures thereof;
D is selected from the group consisting of Cr, Mo, W, Mn, Re, any mixtures thereof; and
wherein
a, b, c and d are 0 to 1; with the proviso that c and d cannot both be equal to 0; and
wherein
x represents the number of oxygens required to satisfy the valence requirements of the other elements present in the catalyst.

The oxide complex catalyst can be any catalyst delineated by the general formula above with respect to the components of the catalyst. Preferred are those catalysts wherein A is one or more of Co and Ni and wherein B is one or more of Cr and Re. Especially preferred are those catalysts which contain both Ru and Fe.

The exact chemical nature of this oxide complex catalyst is not known. This catalyst may be a mixture of oxides, for example, or an oxide complex of all the contained elements. In any event, this type of catalyst is generally known in the art.

The oxide complex catalyst can be made by techniques which are essentially the same as those techniques described in the art for other oxidation catalysts. (See U.S. Pat. No. 3,642,930, which is herein incorporated by reference.) Even though there are numerous techniques that may be utilized to give acceptable oxide complex catalysts, some of the preferred methods of making these catalysts are described below.

The oxide complex catalysts can be prepared from any mixture of compounds that can give the desired oxide components. Preferably, the catalysts are prepared by coprecipitating decomposable salts such as nitrates, acetates, halides and/or oxides. These catalysts are effective in both the calcined and uncalcined form. Other known oxide complex catalyst preparation techniques, however, can be employed.

Active catalytic ruthenium and/or iron metal is also effective in the instant process. These catalysts can be prepared by any of the well known techniques available in the art. (See U.S. Pat. No. 3,784,617, which is herein incorporated by reference.) For example, the active catalytic metal can be prepared from any material that can be at least partially reduced to give the desired metal.

Preferably, the metallic catalyst is prepared by heat treating and hydrogen reducing a decomposable metal salt, e.g. nitrate, acetate, halide, etc.

Although the above technique for preparing a metallic catalyst is preferred, other preparation techniques are known to those of ordinary skill in the art. These alternate preparation techniques are included in the scope of the instant invention.

Both the oxide complex and active catalytic metal catalysts can be in the supported, unsupported or coated form. Preferred support materials are silica, $ZrO_2$, alumina, phosphates, silica-alumina and zeolites. Any other known support material can be used which is stable under the reaction conditions to be encountered in the use of the catalyst. In the supported form, the support preferably comprises 5% to 95% by weight of the catalyst, preferably 10% to 60% by weight of the catalyst. In the coated catalyst form the inert core material is preferably in the range of from about 20% to 99% by weight of the catalyst.

Recovery

The reaction product obtained upon completion of the reaction is normally in the form of a liquid and composed primarily of unreacted reactant and heterocyclic compounds. This reaction product can be subjected to suitable known separation techniques, e.g. solvent extraction or fractional distillation, to yield the desired end product.

The reaction mixture can be made free of catalyst by filtration. The heterocyclic compound can then be separated from the reactant by fractional distillation. It is preferable to conduct this distillation under reduced pressure.

The heterocyclic compounds produced by this process are useful as precursors to polymers.

SPECIFIC EMBODIMENTS

In order to more thoroughly illustrate the present invention, the following working examples are presented. In these example, conversion and yield are defined as follows:

$$\text{Conv.} = \frac{\text{Moles Cyanoester Reacted}}{\text{Moles Cyanoester Fed}} \times 100$$

$$\text{Yield} = \frac{\text{Moles Product}}{\text{Moles Cyanoester Fed}} \times 100$$

The hydrogenation products were analyzed by gas chromatography using a Hewlett-Packard 5750. The examples were performed as follows:

EXAMPLE 1—Hydrogenation Using Metallic Catalysts

Methyl-3-cyanopropionate was hydrogenated in the presence of a metallic ruthenium catalyst. This catalyst was prepared as follows. 5 grams of $RuCl_3.3H_2O$ and 250 ml. of distilled $H_2O$ were reduced with 6.5 grams of $NaBH_4$ and 250 ml. of $H_2O$ slowly over the course of one hour. This solid was then washed with $H_2O$ and MeOH and then dried in a nitrogen atmosphere. 0.15 grams of this metallic ruthenium catalyst was placed in a 300 ml. Parr autoclave. 1.0 gram of cyanoester and 49.0 grams of methanol were also placed inside the autoclave. The autoclave was sealed, flushed twice with 200 psi of hydrogen, and then charged to 700 psi. The autoclave was heated to 100° C. and pressure adjustments, if necessary, were made. The reaction then proceeded for 1 hour. Following this, the autoclave was cooled and vented and the liquid analyzed. A 62% yield of pyrrolidone was obtained.

EXPERIMENTS 2 and 3—Hydrogenation Using Simple Ruthenium and Iron Oxide Catalysts

EXAMPLE 2—$RuO_2$ Catalyst

An $RuO_2$ catalyst was purchased from Alfa/Ventron of Danvers, Massachusetts. This catalyst was purchased in the form of $RuO_2.H_2O$ and contained 53% ruthenium. 0.5 grams of this catalyst was placed in the experimental apparatus described in Example 1. An 81% yield of pyrrolidone was obtained.

EXAMPLE 3—$Fe_2O_3$ Catalyst

An $Fe_2O_3$ catalyst was purchased from Matheson, Coleman and Bell. 0.5 grams of this catalyst was placed in the experimental apparatus described in Example 1. The conditions were changed so that the reaction proceeded for 90 minutes at 150° C. and 1,200 psi. An 80% yield of pyrrolidone was obtained.

EXAMPLES 4 thru 8—Hydrogenation Using Mixed Oxide Catalysts

EXAMPLE 4—$RuFeO_x$ Catalyst

Methyl-3-cyanopropionate was hydrogenated to pyrrolidone in the presence of an $RuFeO_x$ catalyst. This catalyst was prepared as follows. 2.7 grams of $FeCl_3.6H_2O$ and 2.53 grams of $RuCl_3.XH_2O$ were dissolved in 150 ml. of distilled water and stirred for 30 minutes. A 50% aqueous solution of NaOH was added dropwise to bring the pH up to 8.3. The resulting slurry was heated near boiling for 30 minutes with constant stirring, and then cooled. The pH was rechecked and found to be 7.4. The mixture was filtered and washed thoroughly and then reslurried in 150 ml. of distilled water. This mixture was again filtered and washed. The black solid obtained was dried overnight at 125° C. and then calcined at 250° C. for three hours. Before use, this catalyst was ground to pass 140 mesh.

This catalyst was placed in the experimental apparatus disclosed in Example 1 under the conditions specified in Table I. A 99% yield of pyrrolidone was obtained.

EXAMPLE 5—$RuCoO_x$ Catalyst

An $RuCoO_x$ catalyst was also used to hydrogenate methyl-3-cyanopropionate. The catalyst preparation disclosed in Example 4 was followed except that 2.38 grams of $CoCl_2.6H_2O$ was used instead of 2.70 grams of $FeCl_3.6H_2O$. This example was also placed in the experimental apparatus of Example 1 under the reaction conditions disclosed in Table I. A 93% yield of pyrrolidone was obtained.

EXAMPLES 6 thru 8—$FeDO_x$ Catalysts

Promoted iron oxide catalysts were prepared by the technique shown in Example 4 and placed in the experimental apparatus of Example 1 under the reaction conditions shown in Table I. The results of these experiments are also shown in Table I.

EXAMPLES 9 and 10—Hydrogenation Using Catalysts Containing Various Ru/Fe Ratios

EXAMPLE 9—$RuFe_2O_x$ Catalyst

An $RuFe_2O_x$ catalyst was prepared by the catalyst preparation disclosed in Example 4 except that 1.27 grams of $RuCl_3.XH_2O$ was used instead of 2.53 grams of $RuCl_3.XH_2O$. This catalyst was placed into the experimental apparatus disclosed in Example 1 under the reaction conditions specified in Table I. A 45% yield of pyrrolidone was obtained.

EXAMPLE 10—Ru₂FeO$_x$ Catalyst

An Ru$_2$FeO$_x$ catalyst was obtained by the catalyst preparation disclosed in Example 4 except that 1.35 grams of FeCl$_3$.6H$_2$O was used instead of 2.70 grams of FeCl$_3$.6H$_2$O. This catalyst was placed into the experimental apparatus of Example 1 under the conditions disclosed in Table I. An 88% yield of pyrrolidone was obtained.

TABLE I

Hydrogenation of Methyl-3-Cyanopropionate
in an Autoclave in the presence of Mixed Oxide Catalysts Temperature - 100° C.    Reaction Time - 7 Hours
Pressure - 840 psi H$_2$    Ester:Catalyst Ratio (Molar) - 50:1

| Example | Catalyst | Yield of Pyrrolidone (%) |
|---|---|---|
| 4 | RuFeO$_x$ | 99 |
| 5 | RuCoO$_x$ | 93 |
| 6 | FeNiO$_x$ | 34 |
| 7 | FeCoO$_x$ | 33 |
| 8 | FeRhO$_x$ | 65 |
| 9 | RuFe$_2$O$_x$ | 45 |
| 10 | Ru$_2$FeO$_x$ | 88 |

EXAMPLES 11 thru 14—Hydrogenation Using RuFeO$_x$ Catalyst Under Various Process Conditions The catalyst prepared in Example 4 was placed in the experimental apparatus of Example 1 under the reaction conditions disclosed in Table II. The yield of pyrrolidone for each of these examples is also disclosed in Table II.

EXAMPLES 15 thru 16—Hydrogenation Using RuFeO$_x$ Catalyst at Various Catalyst Concentrations The RuFeO$_x$ catalyst prepared in Example 4 was placed into the experimental apparatus of Example 1 for 2 hours at 100° C. and 840 psi. The yield of pyrrolidone for each of these examples is disclosed in Table II.

TABLE II

Hydrogenation of Methyl-3-cyanopropionate in an
Autoclave Under Various Process Conditions Catalyst: RuFeO$_x$

| Example | Ester:Catalyst Ratio (Molar) | Temp. (°C.) | Pressure (psi H$_2$) | Reaction Time | Pyrrolidone (%) |
|---|---|---|---|---|---|
| 11* | 50:1 | 100 | 840 | 7 | 99 |
| 12 | 50:1 | 150 | 840 | 4 | 96 |
| 13 | 50:1 | 100 | 1,300 | 4 | 99 |
| 14 | 50:1 | 100 | 840 | 7 | 81 |
| 15 | 8.45:1 | 100 | 840 | 2 | 81 |
| 16 | 1.74:1 | 100 | 840 | 2 | 93 |

*This catalyst was not calcined.

EXAMPLES 17 thru 21—Hydrogenation Using a Supported RuFeO$_x$ Catalyst

A supported RuFeO$_2$ catalyst was prepared as follows. About 10 grams of the dried and calcined RuFeO$_x$ oxide from Example 4 was ground to 170 mesh and slurried in 15 ml. of water. To this was added appropriate amounts of a 40% Nalco silica solution. The solution was kept thoroughly stirred as it was heated to drive off water. When the mixture reached the consistency of toothpaste, it was put in an oven at 125° C. for 15 hours. It was then calcined at 325° C. for 3 hours. The catalyst was removed from the oven and ground to 10 to 80 mesh particles.

The above catalyst was placed in a continuous flow reactor. The continuous flow reaction system used a 20 cc. fixed-bed reactor with both gas and liquid feed inlets. This reactor was packed with 20 cc. of catalyst. The system was then charged with hydrogen to 1,000 psi, and hydrogen was allowed to pass through the catalyst bed while it was heated to 125° C. When the desired temperature was reached, the system was left to equilibrate for ½ hour. The liquid feed, a 2% solution of cyanoester and methanol, was then pumped in at the appropriate rate and the product was trapped in a cooled collection vessel. The outlet gas was passed through a cooled water scrubber to collect any methanol vapor not condensed with the product. The temperature inside the reactor was monitored continuously with a thermocouple placed 2½ inches from the bottom of the catalyst bed. At the completion of the run, the liquid feed was stopped but hydrogen continued to flow for ½ hour. At that point, the gas was turned off, the reactor was cooled and vented, and the liquid product was analyzed. The results are shown in Table III.

TABLE III

Hydrogenation of Methyl-3-Cyanopropionate in a
Continuous Flow Reaction at Various Catalyst Loading Levels Temperature - 125° C.
Pressure - 1,000 psi H$_2$
Catalyst - RuFeO$_x$ - silica (20 cc.)

| Example | Wt. % Catalyst on Silica | Feed Rate of Ester (cc/Hr) | Yield of Pyrrolidone (%) |
|---|---|---|---|
| 17 | 5 | 17.5 | 65 |
| 18 | 5 | 35.0 | 58 |
| 19 | 30 | 35.0 | 67 |
| 20 | 50 | 35.0 | 74 |
| 21 | 90 | 35.0 | 55 |

EXAMPLE 22—Hydrogenation of Methyl-5-cyanovalerate Using RuFeO$_x$ Catalyst

The RuFeO$_x$ catalyst prepared in Example 4 was placed into the autoclave experimental apparatus described in Example 1. 1.0 gram of methyl-5-cyanovalerate was placed in this apparatus and the reaction proceeded for 7 hours at 840 psi and 100° C. The polar ester/catalyst ratio was 50/1. A 35% yield of caprolactam was obtained.

Although only a few embodiments of the present invention have been specifically described above, it should be appreciated that many additions and modifications can be made without departing from the spirit and scope of the invention. These and all other modifications are intended to be included within the scope of the present invention, which is to be limited only by the following claims:

We claim:

1. A process for producing a five, six or seven-membered saturated nitrogen containing heterocyclic compound comprising contacting a beta, gamma or delta cyano-ester with hydrogen at a temperature in the range of about 50° C. to about 200° C and a pressure in the range of about 100 psi to about 2000 psi in the presence of a catalyst selected from metallic ruthenium, iron and mixtures thereof; wherein said heterocyclic compound has the following structure:

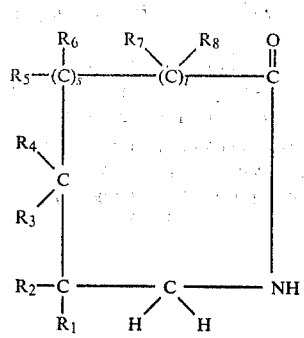

and wherein said cyanoester has the following structure:

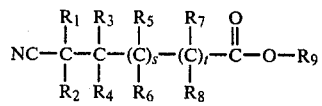

wherein s and t are 0 or 1; and
wherein $R_1$, $R_2$, $R_3$, $R_4$, $R_5$, $R_6$, $R_7$ and $R_8$ are each independently selected from:
  (1) hydrogen;
  (2) $C_{1-4}$ alkyl;
  (3) —$(CH_2)_n$—O—$(CH_2)_r$—H, wherein n and r are each independently 0–4;

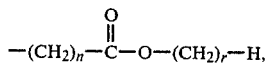 (4)

wherein n and r are each independently 0–4; and
wherein $R_9$ is selected from:
  (1) $C_{1-30}$ alkyls; and
  (2) carbocyclic radicals containing up to 30 carbon atoms.

2. The process of claim 1 wherein s and t are both 0.
3. The process of claim 1 wherein s and t are both 1.
4. The process of claim 1 wherein s is 1 and t is 0.
5. The process of claim 1 wherein $R_1$, $R_2$, $R_3$, $R_4$, $R_5$, $R_6$, $R_7$ and $R_8$ are each independently selected from hydrogen and methyl.
6. The process of claim 1 wherein $R_9$ is selected from the group consisting of $C_{1-4}$ alkyl and phenyl.
7. The process of claim 1 wherein said process contains at least two moles of hydrogen per mole of cyanoester.
8. A process for producing a five, six or seven-membered saturated nitrogen containing heterocyclic compound comprising contacting a beta, gamma or delta-cyanoester with hydrogen at a temperature in the range of about 50° C. to about 200° C. and a pressure in the range of about 100 psi to about 2000 psi in the presence of a catalyst represented by the formula:

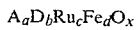

wherein
  A is selected from the group consisting of Co, Ni, Rh, Pd, Os, Ir, Pt and mixtures thereof;
  D is selected from the group consisting of Cr, Mo, W, Mn, Re, any mixtures thereof; and
wherein
  a, b, c and d are 0 to 1; with the proviso that c and d cannot both be equal to 0; and wherein
  x represents the number of oxygens required to satisfy the valence requirements of the other elements present in the catalyst;
wherein said heterocyclic compound has the following structure:

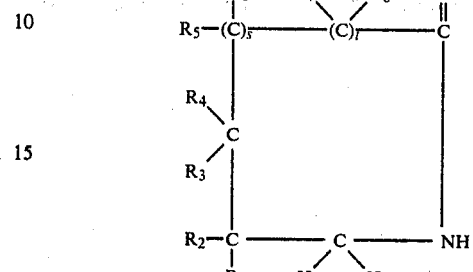

and wherein said cyanoester has the following structure:

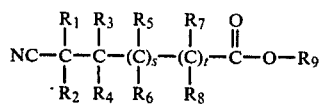

wherein s and t are 0 or 1; and
wherein $R_1$, $R_2$, $R_3$, $R_4$, $R_5$, $R_6$, $R_7$ and $R_8$ are each independently selected from:
  (1) hydrogen;
  (2) $C_{1-4}$ alkyl;
  (3) —$(CH_2)_n$—O—$(CH_2)_r$—H, wherein n and r are each independently 0–4;

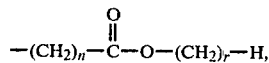 (4)

wherein n and r are each independently 0–4; and
wherein $R_9$ is selected from:
  (1) $C_{1-30}$ alkyls; and
  (2) carbocyclic radicals containing up to 30 carbon atoms.

9. The process of claim 8 wherein d is 0.
10. The process of claim 8 wherein c is 0.
11. The process of claim 8 wherein a is greater than 0.
12. The process of claim 11 wherein A is at least one of Co and Ni.
13. The process of claim 8 wherein b is greater than 0.
14. The process of claim 13 wherein D is at least one of Cr and Re.
15. The process of claim 8 wherein at least 50 mole % of the active catalyst component is Ru.
16. The process of claim 8 wherein c and d are both greater than 0.
17. The process of claim 8 wherein s and t are both 0.
18. The process of claim 8 wherein s and t are both 1.
19. The process of claim 8 wherein s is 1 and t is 0.
20. The process of claim 8 wherein $R_1$, $R_2$, $R_3$, $R_4$, $R_5$, $R_6$, $R_7$ and $R_8$ are each independently selected from hydrogen and methyl.
21. The process of claim 8 wherein $R_9$ is selected from the group consisting of $C_{1-4}$ alkyl and phenyl.

22. The process of claim 8 wherein said cyanoester is methyl-3-cyanopropionate and wherein said heterocyclic compound produced is pyrrolidone.

23. The process of claim 8 wherein said cyanoester is methyl-15-cyanovalerate and wherein said heterocyclic compound produced is caprolactam.

24. The process of claim 7 wherein said process contains at least two moles of hydrogen per mole of cyanoester.

25. The process of claim 1 wherein said cyanoester is methyl-3-cyanopropionate and wherein said heterocyclic compound produced is pyrrolidone.

26. The process of claim 1 wherein said cyanoester is methyl-15-cyanovalerate and wherein said heterocyclic compound produced is caprolactam.

* * * * *